United States Patent [19]
Baran et al.

[11] 3,971,827
[45] July 27, 1976

[54] MANUFACTURE OF POLY-(CIS)-ISOPRENOLS

[75] Inventors: John S. Baran, Winnetka; Barnett S. Pitzele, Skokie, both of Ill.

[73] Assignee: G. D. Searle & Co., Chicago, Ill.

[22] Filed: Sept. 9, 1974

[21] Appl. No.: 504,096

[52] U.S. Cl. ............... 260/526 N; 260/293.51; 260/486 R; 260/631.5; 260/654 R
[51] Int. Cl.$^2$ ............... C07C 57/18; C07C 57/02; C07C 29/02
[58] Field of Search ............... 260/631.5, 526 N

[56] References Cited
UNITED STATES PATENTS

| | | | |
|---|---|---|---|
| 3,654,309 | 4/1972 | Thomas | 260/631.5 |
| 3,658,925 | 4/1972 | Erman et al. | 260/631.5 |
| 3,679,756 | 7/1972 | Kretschmar et al. | 260/631.5 |
| 3,862,212 | 1/1975 | Nomori et al. | 260/631.5 |
| 3,906,035 | 9/1975 | Holan | 260/526 N |

*Primary Examiner*—Joseph E. Evans
*Attorney, Agent, or Firm*—John A. Dhuey

[57] ABSTRACT

γ-Alkylation of 2-butynoic acid utilizing lithium 2,2,6,6-tetramethylpiperidide and 1-bromo-3-methyl-2-butene, followed by esterification of the resulting 7-methyloct-6-en-2-ynoic acid and treatment of the ester with lithium dimethyl cuprate, yields methyl (Z)-3,7-dimethylocta-2,6-dienoate. The ester is reduced to (Z)-3,7-dimethylocta-2,6-dien-1-ol, commonly known as nerol, which is useful as perfume agent.

5 Claims, No Drawings

MANUFACTURE OF POLY-(CIS)-ISOPRENOLS

The present invention is concerned generally with a process for the manufacture of isoprenols. More particularly, it is concerned with a stereoselective process for the manufacture of cis-isoprenols (i.e. (Z)-isoprenols), such as nerol and cis,cis-farnesol. Most particularly, this invention is concerned with an improvement in the process for producing (Z)-isoprenols, which improvement comprises contacting 2-butynoic acid with an alkali metal salt of 2,2,6,6-tetramethylpiperidine thereby promoting γ-alkylation upon further contacting with 1-halo-3-methyl-2-butene or a polyene derivative corresponding of the formula

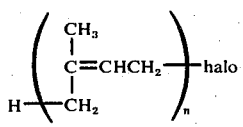

wherein $n$ is a positive integer, i.e. 1, 2, 3, . . .

For the purposes of this invention, alkali metal comprehends lithium, sodium and potassium, with lithium being most especially preferred, and halo comprehends bromo, chloro, iodo and fluoro, with bromo being preferred.

The overall process can be illustrated by the manufacture of nerol, ((Z)-3,7-dimethylocta-2,6-dien-1-ol), which begins with the treatment of 2-butynoic acid with lithium 2,2,6,6-tetramethylpiperidide, followed by alkylation with 1-bromo-3-methyl-2-butene to yield 7-methyloct-6-en-2-ynoic acid as the major product. 2-Ethenylidene-5-methyl-4-hexenoic acid is produced as a minor product in the course of the alkylation. The acids are esterified conveniently with methyl iodide, and treated with morpholine, followed by acid workup, to give a mixture of a major amount of methyl 7-methyloct-6-en-2-ynoate and a minor amount of methyl 2-acetyl-5-methyl-4-hexenoate. The latter compounds are separated by chromatography on a silica gel column using ethyl acetate-n-hexane as eluant. Contacting of the isolated methyl 7-methyloct-6-en-2-ynoate with a mixture of lithium dimethyl cuprate and methyl copper at low temperatures gives methyl (Z)-3,7-dimethylocta-2,6-dienoate, which is reduced to nerol, (Z)-3,7-dimethylocta-2,6-dien-1-ol, for example, with aluminium hydride.

It is apparent that the above product, (Z)-3,7-dimethylocta-2,6-dien-1-ol can be halogenated and utilized as the alkylating agent in the above-described process to produce cis, cis-farnesol, (Z,Z)-3,7,11-trimethyldodeca-2,6,10-trien-1-ol. In like manner the process can be repeated and additional cis-isoprenols prepared, each having one additional cis-isoprenoid unit.

Alkylation of α,β-unsaturated esters and aldehydes generally leads exclusively or preponderantly to α-substituted products. Thus, it is most surprising to discover that 2-butynoic acid, when treated sequentially with an alkali metal salt of 2,2,6,6-tetramethylpiperidine and an alkylating agent, yields γ-alkylated products with a ratio of β-alkylated product to α-alkylated product of greater than 2:1.

The addition of the alkali metal salt of 2,2,6,6-tetramethylpiperidine preferably is carried out at low temperatures, for example, $-120°$ to $-40°C$. A temperature range of $-100°$ to $-60°C$. especially is preferred. An especially preferred solvent system for practicing the invention is a mixture of hexamethyl phosphoramide and tetrahydrofuran, although other solvents compatible with the reactants can be substituted.

An added aspect of this invention is a facile separation of the γ-alkylated and α-alkylated products. Generally those products are very difficult to separate by physical means. However, it has been found that esterification of the acid alkylation products and treatment of the mixture with morpholine converts the allene (i.e. the α-alkylated by-product) to a ketone while leaving the ene-yne ester (i.e. the γ-alkylated product) unreacted. Those materials then can be separated conveniently by column chromatography.

For example, a mixture of 7-methyloct-6-en-2-ynoic acid and 2-ethenylidene-5-methyl-4-hexenoic acid is esterified with methyl iodide, then treated with morpholine in ether, followed by aqueous acid, to yield a mixture of methyl 7-methyloct-6-en-2-ynoate and methyl 2-acetyl-5-methyl-4-hexenoate. Column chromatography, utilizing silica gel with ethyl acetate-hexane as eluent, affords firstly the desired methyl 7-methyloct-6-en-2-yanoate and then the undesired by-product.

The compounds produced in accordance with the instant invention are useful as perfume agents in view of their pleasant odors.

The invention will appear more fully from the examples which follow. They are not to be construed as limiting the invention as variations in materials and methods will be apparent to those skilled in the art without departing from the spirit or scope of this invention. In the examples temperatures are given in degrees Centigrade (°C.).

EXAMPLE 1

25 Grams of distilled 2,2,6,6-tetramethylpiperidine is added, under a nitrogen atmosphere, to 500 milliliters of dry, freshly distilled tetrahydrofuran. The reaction mixture is cooled in a Dry Ice-acetone bath to $-70°$, and 75 ml. of a 2.14 N n-butyl lithium in hexane solution is added over a one-minute interval. The reaction mixture is cooled again down to $-70°$ by the addition of liquid nitrogen to the cold bath, and 7.0 grams of 2-butynoic acid, dissolved in 70 ml. of distilled hexamethylphosphoramide, is added slowly, keeping the reaction temperature at or below $-60°$. After the addition is complete, the reaction mixture is cooled to about $-90°$ and 12.5 grams of 1-bromo-3-methyl-2-butene is added in one portion. The reaction temperature is maintained at about $-70°$ for approximately 2 hours. Then 10 ml. of methanol is added, and the mixture is warmed to room temperature and evaporated at low pressure until about 80 ml. of solution remains. Then 300 ml. of dimethylformamide and 75 ml. of methyl iodide is added, and the mixture is allowed to stand for an additional 3 hours. The reaction mixture is poured into 1.5 liters of water and the organic layer is removed and retained. The aqueous layer is washed with 200 ml. of pentane, and then with two 100 ml. portions of pentane. The organic fractions are combined, washed with cold 2.6 N hydrochloric acid, then with water, and diluted with sodium bisulphite to remove remaining iodine. The organic layer further is washed with water, saturated sodium bicarbonate, and then with saturated sodium chloride. The organic layer is dried over sodium sulphate, filtered and the pentane solvent is evaporated at low pressure to yield a mixture of methyl 7-methyloct-6-en-2-ynoate as the major product and methyl-2-ethenylidene-5-methyl-4-hexenoate as the minor product.

EXAMPLE 2

The alkylation product produced in Example 1 is dissolved in 200 ml. of ethyl ether, and 35 ml. of morpholine is added. The mixture is stirred periodically and, after 1.5 hours, it is poured into cold 4 N hydrochloric acid and extracted with pentane. The organic fractions are washed successively with water, saturated sodium bicarbonate and saturated sodium chloride. The organic phase then is dried over sodium sulphate and filtered, and the solvent is evaporated under low pressure. The residual oil is chromatographed over silica gel using a mixture of ethyl acetate-n-hexane as eluant. Desired methyl 7-methyloct-6-en-2-ynoate is eluted with 3% ethyl acetate-97% hexane. The methyl 2-acetyl-5-methyl-4-hexanoate which follows is discarded.

EXAMPLE 3

To 80 ml. of freshly distilled dry tetrahydrofuran is added 5.75 grams of copper iodide. The suspension is cooled to about −6° and placed under a nitrogen atmosphere. Then 24.6 ml. of a 2.22 N methyl lithium in ether solution is added carefully, keeping the temperature at or below +20°. After all of the methyl lithium is added, the reaction mixture is cooled to −70°, and 0.5 part of methyl 7-methyloct-6-en-2-ynoate is added in one portion. The reaction is allowed to continue for about 6 hours at −70°, and then 10 ml. of methanol is added dropwise. The reaction mixture is allowed to warm to room temperature. Then it is poured into 400 ml. of a 1:1 mixture of saturated sodium chloride and pentane, mixed well and filtered through diatomaceous earth. The organic phase is separated, washed with saturated sodium chloride and evaporated under reduced pressure to give a mixture of methyl (Z)-3,7-dimethylocta-2,6-dienoate and methyl (E)-3,7-dimethylocta-2,6-dienoate in a ratio of 12.4:1.

EXAMPLE 4

To 10 ml. of 1 M lithium aluminum hydride in tetrahydrofuran, cooled to 0°, is added, dropwise, 0.28 ml. of 18 M sulfuric acid. The addition should be made at a rate such that the temperature remains at or below about +15°. After the addition is complete, the reaction mixture is stirred for 20 minutes and 0.55 grams of methyl (Z)-3,7-dimethylocta-2,6-dienoate is added. The reaction is allowed to proceed for about 3 hours while keeping the temperature between 0° and +5°. Then 20 ml. of ethyl ether is added, followed successively by 0.4 ml. of water, 0.4 ml. of a 15% sodium hydroxide water solution, and 1.2 ml. of water. The mixture then is filtered and the solid remaining is washed with ethyl ether. The organic filtrate is dried over sodium sulphate, filtered and evaporated under reduced pressure to yield, as an oil, (Z)-3,7-dimethylocta-2,6-dien-1-ol.

EXAMPLE 5

A stirred solution of 51.4 grams of (Z)-3,7-dimethyl-2,6-octadien-1-ol in 400 milliliters of dry ethyl ether, protected from light, is treated with 29.8 grams of phosphorous tribromide, dropwise, over a ½ hour period. The mixture is refluxed for about 2.5 hours, then cooled, poured on ice water and extracted with ether. The ethereal extract is washed with sodium bicarbonate, then with water and dried over sodium sulfate. Solvent is removed under reduced pressure to yield (Z)-1-bromo-3,7-dimethyl-2,6-octadiene.

EXAMPLE 6

An equivalent quantity of (Z)-1-bromo-3,7-dimethyl-2,6-octadiene is substituted in Example 1, and the procedures of Examples 1, 2, 3 and 4 successively are followed to yield (Z,Z)-farnesol, (Z,Z)-3,7,11-trimethyldodeca-2,6,10-trien-1-ol.

What is claimed is:

1. A process for the production of γ-alkylated acids which comprises the steps of successively contacting 2-butynoic acid with an alkali metal salt of 2,2,6,6-tetramethylpiperidine and a halo-polyene of the formula

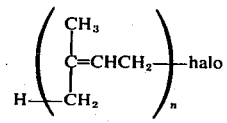

wherein n is 1 or 2.

2. A process as in claim 1 wherein the alkali metal is lithium.

3. A process as in claim 2 wherein n is 1 and halo is bromo.

4. A process as in claim 2 wherein n is 2 and halo is bromo.

5. A process for the production of cis-isoprenol which comprises the steps of:
  a. successively contacting 2-butynoic acid with an alkali metal salt of 2,2,6,6-tetramethylpiperidine and 1-bromo-3-methyl-2-butene to produce 7-methyloct-6-en-2-ynoic acid as the major product and 2-ethenylidene-5-methyl-4-hexenoic acid as the minor product;
  b. esterifying the acids of step a to produce the corresponding methyl 7-methyloct-6-en-2-ynoate and methyl-2-acetyl-5-methyl-4-hexenoate;
  c. chromatograhically separating the compounds of step b to isolate methyl 7-methyloct-6-en-2-ynoate;
  d. contacting the isolated product of step c with lithium dimethyl cuprate and methyl copper to produce methyl (Z)-3,7-dimethylocta-2,6-dienoate; and
  e. reducing the product of step d to produce (Z)-3,7-dimethylocta-2,6-dien-1-ol.

* * * * *

UNITED STATES PATENT AND TRADEMARK OFFICE
CERTIFICATE OF CORRECTION

PATENT NO. : 3,971,827
DATED : July 27, 1976
INVENTOR(S) : John S. Baran & Barnett S. Pitzele It is certified that error appears in the above-identified patent and that said Letters Patent are hereby corrected as shown below:

Column 1, line 64, "$\beta$-alkylated" should read -- $\gamma$-alkylated --.

Signed and Sealed this

Eighteenth Day of January 1977

[SEAL]

Attest:

RUTH C. MASON
*Attesting Officer*

C. MARSHALL DANN
*Commissioner of Patents and Trademarks*